US011033589B2

(12) United States Patent
Daniels et al.

(10) Patent No.: US 11,033,589 B2
(45) Date of Patent: Jun. 15, 2021

(54) ORAL DOSAGE FORM

(71) Applicant: Symrise AG, Holzminden (DE)

(72) Inventors: Rolf Daniels, Rottenburg a.N. (DE);
Anja Hoffmann, Dettingen/Erms (DE);
Marcus Götz, Oberweser (DE); Jörg Fischer, Brakel (DE); Kerstin Holmgren, Helsingborg (SE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 16/574,402

(22) Filed: Sep. 18, 2019

(65) Prior Publication Data

US 2020/0078422 A1 Mar. 12, 2020

Related U.S. Application Data

(63) Continuation of application No. 15/261,042, filed on Sep. 9, 2016, now abandoned.

(30) Foreign Application Priority Data

Sep. 11, 2015 (EP) .................................. 15 184 849
Nov. 10, 2015 (EP) .................................. 15 193 826

(51) Int. Cl.
| A61K 35/747 | (2015.01) |
| A61K 9/00 | (2006.01) |
| A61K 9/20 | (2006.01) |
| A61K 35/00 | (2006.01) |
| G01N 33/50 | (2006.01) |
| A61K 9/19 | (2006.01) |

(52) U.S. Cl.
CPC ............ *A61K 35/747* (2013.01); *A61K 9/006* (2013.01); *A61K 9/0056* (2013.01); *A61K 9/205* (2013.01); *A61K 9/2009* (2013.01); *A61K 9/2013* (2013.01); *A61K 9/2018* (2013.01); *A61K 9/2027* (2013.01); *A61K 9/2045* (2013.01); *A61K 9/2054* (2013.01); *A61K 9/2059* (2013.01); *A61K 9/2063* (2013.01); *A61K 9/2068* (2013.01); *A61K 9/2095* (2013.01); *G01N 33/5088* (2013.01); *A61K 9/19* (2013.01); *A61K 2035/115* (2013.01)

(58) Field of Classification Search
None
See application file for complete search history.

(56) References Cited

U.S. PATENT DOCUMENTS

| 4,518,615 | A | 5/1985 | Cherukuri et al. |
| 5,093,136 | A | 3/1992 | Panhorst et al. |
| 5,266,336 | A | 11/1993 | McGrew et al. |
| 5,601,858 | A | 2/1997 | Mansukhani et al. |
| 5,741,524 | A | 4/1998 | Staniforth |
| 6,986,709 | B2 | 1/2006 | Hughs-Baird et al. |
| 7,122,198 | B1 | 10/2006 | Singh |
| 8,545,881 | B2 | 10/2013 | Venkatesh |
| 2003/0181501 | A1 | 9/2003 | Le |
| 2003/0215502 | A1 | 11/2003 | Pruss |
| 2006/0046958 | A1 | 3/2006 | Bakhit et al. |
| 2007/0292508 | A1 | 12/2007 | Szamosi |
| 2009/0110717 | A1 | 4/2009 | Singh et al. |
| 2009/0117056 | A1* | 5/2009 | Hodal, Jr. ............ A61K 35/747 424/48 |
| 2010/0063110 | A1 | 3/2010 | Meyer et al. |
| 2011/0008493 | A1 | 1/2011 | Zorea |
| 2011/0028431 | A1 | 2/2011 | Zerbe et al. |
| 2011/0256229 | A1 | 10/2011 | Nystrom et al. |
| 2012/0022087 | A1 | 1/2012 | Rimkus |
| 2012/0322663 | A1 | 12/2012 | Harel |
| 2013/0136826 | A1 | 5/2013 | Penhasi |
| 2013/0337022 | A1 | 12/2013 | Pillay et al. |
| 2014/0234212 | A1 | 8/2014 | Goldberg et al. |

FOREIGN PATENT DOCUMENTS

| CN | 101606566 A | 12/2009 |
| EP | 0242325 A2 | 3/1987 |
| EP | 2420580 A1 | 2/2012 |
| JP | 2001039861 A * | 2/2001 |
| WO | 2014152338 A1 | 9/2014 |

OTHER PUBLICATIONS

Jorgensen "Use of Probiotics in Future Prevention and Treatment of Oral Infections" A.M.L. Pedersen (ed.), Oral Infections and General Health: From Molecule to Chairside Cham:Springer International Publishing Switzerland 2016 p. 125-13 (Year: 2016).*
Iwamoto et al. Oral Surgery, Oral Medicine, Oral Pathology and Oral Radiology 2010 110:201-208 (Year: 2010).*
Shirwaikar et al. Indian Journal of Pharmaceutical Sciences 2004 66(4):422-426 (Year: 2004).*
Benjamin Public Health Reports 2010 125:158-159 (Year: 2010).*
Stahl www.gea.com/en/stories/comparing-granulation-techniques. jsp 13 pages (Year: 2014).*
Klayraung et al, "Development of tablets containing probiotics: Effects of formulation and processing parameters on bacterial viability," International Journal of Pharmaceutics vol. 370, Nos. 1-2, Mar. 31, 2009, pp. 54-60.

(Continued)

*Primary Examiner* — Robert A Wax
*Assistant Examiner* — Caralynne E Helm
(74) *Attorney, Agent, or Firm* — Dilworth & Barrese, LLP

(57) ABSTRACT

The present invention is in the field of delivering an active substance to the oral cavity and relates to mucoadhesive active composition and corresponding mucoadhesive dosage form, which can deliver an active substance within the oral cavity, especially an orodispersible tablet for delivering probiotic substance. The present invention also relates to a method of producing the said composition and a method of processing the composition into a mucoadhesive dosage form, especially an orodispersible tablet. The present invention moreover relates to a system and a method for testing the mucoadhesion of a dosage form.

5 Claims, 1 Drawing Sheet

(56) References Cited

OTHER PUBLICATIONS

Carvalho et al., "Mucoadhesive drug delivery systems", Braz. J. Pharm. Sci. 46:(1), Sao Paulo Jan./Mar. 2010; on-line version ISSN 2175-9790 dated Aug. 15, 2017, 1-20.
European Search Report from EP 16 18 8095 dated Jan. 10, 2017.
European Search Report from EP 15193826.3-1455 dated Mar. 3, 2016.
Examination from EP 16 188 095.0.
ICPI Workshop 2011 Reference www.fs.us/rl/fire. . . .

\* cited by examiner

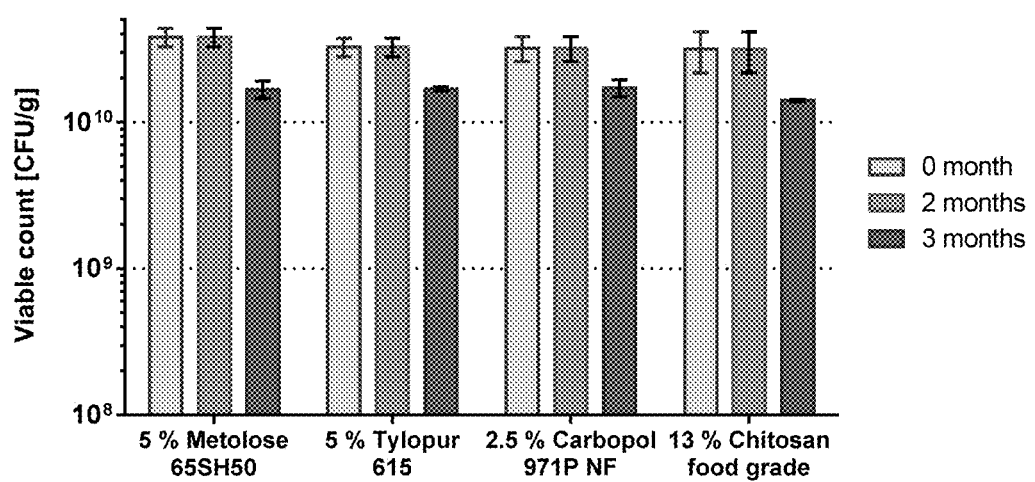

ORAL DOSAGE FORM

This application is a continuation application of U.S. patent application Ser. No. 15/261,042 filed on Sep. 9, 2016, which claims priority to EP 15184849.6 filed on Sep. 11, 2015 and EP 15193826.3 filed Nov. 10, 2015.

FIELD OF INVENTION

The present invention is in the field of delivering an active substance to the oral cavity and relates to mucoadhesive active composition and corresponding mucoadhesive dosage form, which can deliver an active substance within the oral cavity, especially an orodispersible tablet for delivering probiotic substance. The present invention also relates to a method of producing the said composition and a method of processing the composition into a mucoadhesive dosage form, especially an orodispersible tablet. The present invention moreover relates to a system and a method for testing the mucoadhesion of a dosage form.

STATE OF THE ART

Oral delivery is the method of swallowing an active substance with the intention of releasing it into the gastro-intestinal (GI) tract of humans and animals. The GI tract comprises mainly the stomach, small bowl and large bowel. In the pharmaceutical/health care industry oral delivery is the most commonly used method and a highly favored route of an active substance administration due to the factors such as low cost, the ease and avoidance of pain upon administration, as well as a decrease in the risk of infections that are associated with parenteral dosage forms. Furthermore, the relatively large available fluid volume, the increased mucosal area available for absorption and the profuse blood supply to the gastric mucosa aids the absorption of many drugs.

However, poor solubility, stability, and bio-availability of many active substances make achieving therapeutic levels via the GI tract challenging. Oral delivery must overcome numerous hurdles, including the acidic gastric environment and the continuous secretion of mucus that protects the GI tract.

In order to overcome the above-mentioned problems associated with the oral delivery and realize more effective and convenient administration of an active substance, many researches have been focused on the development of a new delivery system within the oral mucosal cavity.

Unlike the described traditional oral dosage forms in which the active ingredient is delivered to the GI tract of the patient/consumer for absorption of the active agents through the stomach or intestinal epithelium, buccal/sublingual dosage forms are intended to be held in the mouth or under the tongue until the contained active substance have been completely released in the mouth.

It is obvious that the key problem of administration via buccal and/or sublingual dosage forms is that physiologically and pharmacologically active substances, edible cosmetics as well as foodstuffs, especially those that cannot rapidly interact with the oral mucosa may be washed away in substantial proportion because of the continuous secretion of saliva in the oral cavity. Suitable buccal and/or sublingual dosage forms must remain in contact with the oral mucosa for a time sufficient for interaction of the contained active substances with the oral mucosa. Hence it is necessary to add a mucoadhesive agent to the dosage forms to extend the retention time in the mouth cavity and to increase the persistence of the active substance on the oral mucosa. The relative technologies have been published in the following applications.

US 2014/0234212 A1 (MASSACHUSETTS INSTITUTE OF TECHNOLOGY) disclosed an oral delivery device comprising a mucoadhesive polymetric matrix, nanoparticles dispersing therein and an impermeable backing layer, wherein the active substances are loaded in the nanoparticles. By application the oral delivery device should be placed onto the mucus layer and through the mucoadhesion adhere to the oral epithelium, where the nanoparticles penetrate in the mucosa and controlled release the loaded active substance. The applied methods of the nanoparticles production are all carried out in a solution comprising active substance and the corresponding polymers.

US 2013/0337022 A1 (UNIVERSITY OF THE WITWATERSRAND) referred to a pharmaceutical dosage form comprising a mucoadhesive layer, a water-insoluble layer and an intermediate layer loading active substance, wherein the active substance are in the form of micro- and/or nanostructures and by directed dissolution, suspended or in an emulsion form incorporated into the intermediate layer. The mucoadhesion of the dosage form was evaluated with Texture Analyser by measuring the tensile force required to separate the dosage membrane from a simulated gastric membrane.

US 20110028431 A1 (ZERBE ET AL) related to a direct compression formulation produced by blending a mucoahesive polymer, a pharmaceutically active substance, a disintegrant and other components, then compressing the obtained blend. The obtained compressed formulation can be further made into a solid oral dosage form. By applying the dosage forms the absorption of the active substance through oral mucosa was enhanced and the ingestion of the active substance was reduced.

US 2010/0063110 A1 (MEYER ET AL) published oral disintegrable films comprising alkaline substances, which can disintegrate in the mouth within 1 to 10 minutes and adhere to the buccal mucosa. The mucoadhesiveness of the films were tested with a tensile strength tester.

US 2009/0110717 A1 (SINGH ET AL) concerned a transmucosal disk containing two compartments for administration of an active substance, preferably the active substance is in the inner compartment and the mucoadhesive agent is in the outer compartment. During the application the partial inner compartment and partial outer compartment adhered to the mucosal membrane to deliver the active substance through the buccal mucosa. After the desired effect of the active substance has been achieved, the disk could be easily peeled off.

In this application probiotics will be particularly introduced as one of the most commonly used active substances. Probiotics are live non-toxic digestible microorganisms that can beneficially affect a host by providing: (1) normalization of flora (e.g., suppress PPMs, provide for intestinal mucosal integrity, regulation of bowel movement, IBS, etc.); (2) immunomodulation (e.g., strengthen immunity, alleviate food allergy symptoms, control of IBD, etc.); (3) metabolic effects (e.g., Production of vitamins to improve digestion, minimize lactose intolerance, lower cholesterol, promote bile acid deconjugates, etc.) and many other benefits to improve the host's intestinal microbial balance without causing any diseases.

A probiotics should be delivered in a formulation that is stable when stored. The colony number of bacteria and viability need to be reliable and they must survive the acid and bilious environment in the upper GI tract before they reach the small intestine and colon. Since the quality and content of probiotics have not been regulated, it is difficult to accurately assess their efficacy and safety. Probiotic delivery systems can be categorized into conventional, pharmaceutical formulations, and non-conventional, mainly commercial food-based, products. Despite the great difference between the two systems, the adsorption sites of probiotic locate mostly in the GI tract.

For example in WO 2014152338 A1 an oral delivery system for delivering a probiotic formulation targeted to the ileum and proximal colon of a subject was disclosed, which comprises: a core comprising a probiotic formulation, wherein the probiotic formulation is included in a biodegradable first capsule that is coated with a first enteric coating, and a second capsule sized to include the coated first capsule, wherein the second capsule releases the first capsule in the ileum and once released the first capsule is solubilized in the proximal colon with the release of the probiotic formulation contained therein.

However because of the particular temperature/humidity sensitivity of probiotics and the efficacy depending on their physiology, activity and viability, the production of live bacteria requires expertise and stringent quality controls throughout the process. Only a few companies in the world possess the industrial capability to produce and process live probiotics into a pure, live, stable, and consistent probiotics formulations. Particularly to probiotics formulations for long-lasting delivery within the oral cavity, nearly no companies report relative information and research development.

Hence, based on the known important benefit of probiotics on human healthy through influencing flora in human bodies, the main problem underlying the present invention has been providing mucoadhesive active compositions and corresponding mucoadhesive dosage form, especially an orodispersible tablet for delivering probiotic substances, which can extend the application of probiotics to the oral cavity, thereby preventing or countering gingivitis and periodontitis by various effects such as anti-inflammatory, antibacterial, adherence promotive and microbiota influencing effects in the oral cavity. Another problem solved by the present invention has been producing the said granules and processing the granules into a mucoadhesive dosage form, especially an orodispersible tablet. Besides a further problem underlying the present invention has been supplying a system and a method for testing the mucoadhesion of a dosage form, to evaluate the mucoadhesion of a dosage form and obtain stable and dependable results.

DESCRIPTION OF THE INVENTION

The aim of the invention is to apply live probiotics culture direct in the oral cavity and keep enough amount of probiotics adhere to the oral mucosa to realize the effect of probiotics on the oral healthy. Hence the present invention provide mucoadhesive active granules and corresponding mucoadhesive dosage form processed from these granules, which can delivery active substance within the oral mucosal cavity, especially orodispersible tablets for delivering probiotic substance. The said orodispersible tablets can totally disintegrate within short time and release active and attenuated probiotics, which can fix to the oral mucosa with the help of the components with mucoadhesion.
(i) Mucoadhesive active composition of the present invention comprise
(ii) a mucoadhesive polymer, and
(iii) a solid active agent.

It is surprisingly observed the mucoadhesive active composition of the present invention possess considerable biological activity and better applicability compared with the pure active agent. Besides the claimed compositions also offer potential for industry, that they can as active base material be easily processed into various mucoadhesive oral dosage form, such as tablet or capsule. Stability data of mucoadhesive probiotic orodispersable tablets according to the present invention are provided in FIG. 1.

In the present invention the solid active agent is preferably an anti-inflammatory, corticosteroid, anti-diarrhoeal, opioid, immunosuppressive, antibiotic, antiemetic, antifungal, antiviral, antimalarial, anti-TB drug, antiretroviral, antihypertensive, protein, peptide, chemotherapeutic, diagnostic agent, prebiotic, multivitamin, mineral, trace element, phytonutrient, protein, peptide or the like.

More preferably, the solid active agents used in the present invention are beneficial microorganisms (probiotics) and their derivatives. It should be noted that this is the first time to realize the adhesion of probiotics to the oral mucosa with the help of mucoadhesive polymers.

Probiotics and their Derivatives

In the present invention probiotics are understood as live microorganisms, which possess properties that are useful for the host. According to the FAO/WHO definition, they are "live microorganisms which at appropriate dosage give the host a health advantage". Probiotics are usually ingested as a constituent of fermented foods, to which special live cultures have been added, e.g. yoghurt, soya yoghurt or other probiotic foods. Furthermore, tablets, capsules, powder and sachets are also available, which contain the microorganisms in freeze-dried form.

The preferable probiotics applied according to the present invention are listed as following:
*Lactobacillus plantarum* 299V
*Lactobacillus plantarum* Heal 9 (DSM 15312)
*Lactobacillus plantarum* Heal 52A (Heal 19) (DSM 15313)
*Lactobacillus plantarum* Heal 99 (DSM 15316)
*Lactobacillus fermentum* 35 D [database number not available],
*Lactobacillus fermentum* GOS 51 [database number not available],
*Lactobacillus plantarum* GOS 42 [database number not available],
*Lactobacillus paracasei* GOS 63 [database number not available]

Further to probiotics, derivatives such as heat-treated probiotics, fragments thereof for example epitopes can be formulated as the active agent in the sense of the present invention.

Mucoadhesive Polymers

"Mucoadhesive/Mucoadhesion" is a property of a material that has the ability to adhere to mucosal membranes in the human body. Mucoadhesive polymers preferably used in this invention include hydrophilic polymers and natural gums. Examples of preferred hydrophilic polymers are cellulosic polymers such as hydroxyethyl cellulose, hydroxypropyl cellulose, methyl cellulose, hydroxypropyl methylcellulose, hydroxyethyl methylcellulose, ethylhydroxyethyl cellulose, carboxymethyl cellulose and its salts and mixtures of two or more thereof; vinyl polymers such as polyvinyl acetate, polyvinyl alcohol, polyvinyl pyrrolidone; and acrylic acid polymers and copolymers such as polyacrylic acid and its salts, polycarbophil etc. Natural gums are polysaccharides of natural origin. Examples of some natural gums are carrageenan, konjac, sodium and calcium alginate, agarose, guar, pectin, tragacanth, acacia, arabic, dextran, gellan, xanthan, scleroglucan, hyaluronic acid, chitosan, fenugreek gum, locust bean gum etc. Combinations of the above mucoadhesive polymers may also be employed. Other mucoadhesive polymers or combinations of mucoadhesive polymers may also be used.

The most preferable mucoadhesive polymer in the present invention is selected from group comprising Carbopol 971P NF (polyacryl acid), Tylopur 615 (hypromellose, hydroxypropyl methylcellulose, HPMC), Metolose 65SH50 (hypromellose, hydroxypropyl methylcellulose, HPMC), and Chitosan.

In one preferable embodiment of the present invention the used ratio between a mucoadhesive polymer and a solid active agent is from about 10:1 to about 1:50, preferably from about 2:1 to about 1:20, more preferably from about 1:1 to about 1:10.

In another preferable embodiment the used solid active agent can be firstly granulated, and then mixed with the mucoadhesive polymer. The obtained granules of the solid active agent have a diameter from 50 to 1000 μm.

In another preferable embodiment of the present invention, the mucoadhesive active composition of the present invention can be processed into granules with a diameter from 50 to 1000 μm. Another object of the present invention is a mucoadhesive dosage form, especially an orodispersible tablet for delivering probiotic substance within the oral cavity.

An orodispersible tablet according to the present invention, comprising
(i) mucoadhesive active composition according to the present invention, and
(ii) excipients comprising at least one disintegrant,
(iii) mixed and compressed to form a tablet.

The orodispersible tablet of the invention disintegrates completely within 3 minutes regarding to European Pharmacopoeia measured by the described method "disintegration of tablets and capsules" (2.9.1). In the "Guidance for Industry Orally Disintegrating Tablets" from the FDA a disintegration time of less than 30 seconds is recommended. The released mucoadhesive probiotics granule can adhere to the buccal mucosa.

Orodispersible Tablet

Orodispersible tablets (ODT) are also called as orally disintegrating tablets, mouth-dissolving tablets, rapid-dissolving tablets, fast-disintegrating tablets, fast-melting tablets, and fast-dissolving tablets. Recently, European Pharmacopoeia has used the term orodispersible tablets. ODTs differ from traditional tablets in that they are designed to be dissolved in the oral cavity, for example on the tongue within short time period such as 3 minutes, rather than swallowed as whole. The ODT serves as an alternative dosage form for delivering the active ingredients direct in the oral cavity, and influencing the active site locating in the buccal mucosa.

Excipients

In the present invention excipients may be defined as inactive constituents other than the physiologically and pharmacologically active constituents, edible cosmetics as well as foodstuffs, which are included in the manufacturing process or are contained in a finished pharmaceutical product dosage form. In addition to transporting the active constituents to the site in the body where the drug is intended to exert its action, excipients play an important part in the manufacturing process. They may also be important for keeping the active ingredients from being released too early in the assimilation process. Others help the drug to disintegrate into particles fast enough to release the active principle and still others protect the product's stability so it will be at maximum effectiveness at time of use. In addition, some excipients are used to aid the identification of a drug product. Last, but not least, some excipients are used simply to make the product taste and look better. This improves patient compliance, especially in children. Although technically "inactive" from a therapeutic sense, pharmaceutical excipients are critical and essential components of a modern drug product. In many products, excipients make up the bulk of the total dosage form.

In the present invention the used excipients comprise at least one disintegrant.

Disintegrants

A disintegrant is an excipient which is added to a tablet or a capsule to aid in the breakup of the compacted mass when it is put into a fluid environment. This is especially important for immediate release products where rapid release of active substance is required. The oral dosage forms, especially orodispersible tablets of this invention include disintegrating agents (disintegrants) such as croscarmellose sodium, calcium carboxymethyl cellulose, crospovidone, hydroxypropylcellulose (low substituted), starch, sodium starch glycolate, alginic acid, calcium alginate, bentonite, cellulose, guar galactomannan and the like in amounts sufficient to achieve a desirable and efficient disintegration rate that optimizes release of the physiologically and pharmacologically active substance, edible cosmetics as well as foodstuffs, minimizes consumer's discomfort and inconvenience, or achieves a desired balance of release efficiency and reduced discomfort and/or inconvenience.

In one preferable embodiment of the present invention crospovidone (e.g. Kollidon CL-SF) is used as the disintegrant to produce the orodispersible tablet.

In one preferred embodiment of the present invention the mucoadhesive active composition are present in an amount of from about 0.1 to about 80 wt. %, preferable from about 10 to about 40 wt. % based on the weight of the orodispersible tablet.

In one preferred embodiment of the present invention the disintegrants are present in an amount of from about 1 to about 15 wt. %, preferable from about 2 to about 5 wt. %, based on the weight of the orodispersible tablet.

In a further preferable embodiment obtained orodispersible tablet of the present invention complete disintegrate within about 3 minutes, preferably within about 30 seconds or less.

In one preferred embodiment the mucoadhesive active composition comprises the solid active agent, especially the probiotics in the form of granules. It is obvious to the person skilled in the prior art, that granulation of the used components generally has negative influence on the disintegration e of the obtained orodispersible tablet. Hence the skilled person would avoid granulating the active agent with mucoadhesive polymers, in order to realize effective drug release of an orodispersible tablet. However it has been surprisingly found, that by granulating the active agent, especially probiotics with mucoadhesive polymers, such as hypromellose, poly acrylic acid or chitosan the disintegration time of the obtained orodispersible tablet could be reduced for hypromellose and drastically reduced for poly acrylic acid. Hence the granulation of probiotics and mucoadhesive polymers accelerates tablet disintegration compared to tablets with ungranulated mucoadhesive polymers. Still tablets including granulated chitosan disintegrate fast.

In another further preferable embodiment the mucoadhesive active composition are processed into granules with a diameter from 50 to 1000 µm, preferably from 75 to 700 µm.

The European Pharmacopoeia defines "complete disintegration" as that state in which any residue of the unit, except fragments of insoluble coating or capsule shell, remaining on the screen of the test apparatus is a soft mass having no palpably firm core.

The disintegration time is a very important parameter for orodispersible tablets. The disintegration time of the tablets was measured according to the method described in European Pharmacopoeia (Tablet disintegration (Ph. Eur. 2.9.1)), which is a standard method. For determining the time for disintegration exactly, only one tablet was measured at a time. The temperature of the water was between 35° C. and 39° C. Maximum three tablets were tested per cycle, before changing the water in the beaker completely. A sample size of 6 tablets was measured from every batch. For lyophilisates and in accordance with Ph. Eur., disks were used to ballast the tablets, because they showed a tendency to float due to their low specific gravity.

From a practical standpoint, the oral disintegrating tablet of the invention completely disperse in vitro within the time periods indicated, with a proviso to be made from a strict scientific standpoint, namely that, obviously, components of the tablets that are not soluble in the saliva will not dissolve but rather be dispersed and remain in the solid state.

Besides the disintegrants the excipients used in the orodispersible tablet according to the present invention can further comprise fillers and lubricants.

Fillers

Diluents or fillers are inert ingredients that can significantly affect the chemical and physical properties of the final tablet thus affecting the release profile. Moreover, a binder and filler is often necessary to prepare ODTs by direct compression to achieve sufficient hardness. Cellulose products are typical substances for this purpose. In particular microcrystalline cellulose can be beneficial as it also assists the fast disintegration of ODTs, involving swelling and a wicking effect. Further fillers that may be employed in the compression and oral dosage forms of this invention include water-soluble sugars such as lactose, glucose, sucrose, dextrose, isomalt and sugar alcohols such as lactose mannitol, sorbitol, xylitol, and erythritol. Other water-soluble sugar and sugar alcohols may also be employed and combinations of water-soluble sugar and sugar alcohols may be used. Other fillers that may be employed include, without limitation, calcium sulfate, calcium carbonate, dibasic calcium phosphate, stearic acid, starch, and microcrystalline cellulose. The filler may be present in the orodispersible tablet of the present invention in an amount of from about 10 to about 90 wt % of the orodispersible tablet.

Lubricants

For pharmaceutical operations such as blending, roller compaction, tablet manufacturing, and capsule-filling, lubrication is essential in order to reduce the friction between the surfaces of manufacturing equipment and that of active solids, to prevent ingredients from clumping together as well as to ensure the continuation of an operation. Pharmaceutical lubricants are the agents added to tablet formulations in a very small quantity (usually 0.25%-5.0%, w/w) to improve the processing properties of dosage forms. Lubricants that may be employed in the compression and oral dosage forms of this invention include calcium and magnesium stearate, glycerol dibihenate, glycerol distearate, sodium stearyl fumarate, oleic acid, hydrogenated castor oil, sucrose fatty acid esters, stearic acid, adipic acid, fumaric acid, polyethyleneglycol, sodium benzoate, sodium dodecyl sulfate, poloxamers, and like.

In one preferable embodiment of the present invention the used lubricants is sodium stearyl fumarate (Pruv®).

The mucoadhesive dosage forms of the present invention may further comprise other optional ingredients as desired, including natural and/or artificial sweeteners such as aspartam, taste-masking agents and/or flavorants such as menthol, and colorants (e.g., red iron oxide dye). Antioxidants, stabilizers, solubilizing agents, preservatives, colorants and other processing aids may also be employed as needed or desired to facilitate handling and/or compression into tablets or other oral dosage forms.

Mucoadhesion

Another object of the present invention is a method of producing the mucoadhesive active granules of the present invention, more particularly a method of producing mucoadhesive active granules, comprising (i) mixing a solid active agent and a mucoadhesive polymer with a binder solution to obtain a wetted blend;
(ii) granulating the wetted blend of step (i) to obtain wetted granules;
(iii) drying and sieving the wetted granules of step (ii) to obtain the mucoadhesive active granules.

The solid active agent used in the method is preferably probiotics.

In one preferred embodiment of the present invention the probiotic substance are with a diameter <500 µm, preferably <400 µm, more preferably <300 µm.

The preferable mucoadhesive polymer used in the method is selected from group comprising Carbopol 971P NF (Polyacryl acid), Tylopur 615 (hypromellose, hydroxypropyl methylcellulose, HPMC), Metolose 655H50 (hypromellose, hydroxypropyl methylcellulose, HPMC), and Chitosan.

In one preferable embodiment of the present invention the used ratio between a mucoadhesive polymer and a solid active agent is from about 10:1 to about 1:50, preferably from about 2:1 to about 1:20, more preferably from about 1:1 to about 1:10.

Binders

Binders are agents which are used in pharmaceutical formulations (of solid oral dosage forms) to hold the active ingredient and inactive ingredients together. In the present invention binders are particularly used to bind the solid active agents, especially the probiotics, with the mucoadhesive polymer together. Typical Examples of binder agents are acacia gum, gelatin, polyvinylpyrrolidone and copovidone, polyvinyl alcohol, starch (paste and pre-gelatinized), sodium alginate and alginate derivatives, sorbitol, glucose and other sugars, tragacanth and soluble cellulose derivates like methylcellulose, hydroxypropylmethylcellulose, sodium carboxymethylcellulose and hydroxypropylcellulose, maltodextrin, poly methacrylate copolymers, e.g. ammonio methacrylate copolymer, methacrylic acid methyl methycrylate copolymer, basic butylated methacrylate copolymer, methacrylic acid ethyl acrylate copolymer, cellacefate, hypromellose acetate succinate, hypromellose phthalate, polyvinyl acetate phthalate, polyvinyl alcohol-polyethylene glycol copolymer, shellac. Moreover mucoadhesive polymers can also be used as binder.

The disintegration of tablets produced with granulated Lactobacilli strains disintegrate clearly faster than the pure bacteria. This effect was independent of the used strain.

The preferably used binder in the present invention is anionic methacrylic acid ethyl acrylate copolymer (EUDRAGIT® L-Types).

In one embodiment of the present invention the binders may be dissolved in a solvent, which must be volatile so that it can be removed by drying, and be non-toxic. Typical solvent include water, ethanol and isopropanol either alone or in combination.

In one preferred embodiment of the present invention the binders is applied in amounts of 0.5-20 wt. %, preferably from 2-15 wt. % with respect to the solid active agents.

In another embodiment of the present invention a solid active agent may be firstly mixed with a mucoadhesive polymer under dry condition, for example with the addition of desiccant bags, to obtain a dry blend.

In another preferred embodiment of the present invention the obtained dry blend is tempered to about from 15 to 25° C., preferably to 20° C. accompanied by the constant flow of nitrogen. Subsequently under stirring a binder solution is added into the dry blend.

In a further preferred embodiment of the present invention the wetted granules may be sieved previous to the drying to remove big granules with a diameter >3500 μm, preferably >1000 μm, more preferably >700 μm.

Besides in one preferred embodiment of the present invention the drying of the wetted granules is carried out in the desiccator by flushing with compressed air.

The mucoadhesive active granules produced according to the method of the present invention is preferably with a water activity $(a_w)$<0.1. In the present invention water activity is defined as the ratio of the vapour pressure of water in a material to the vapour pressure of pure water at the same temperature.

In one preferred embodiment of the present invention dried granules are sieved finally to remove big granules with a diameter >1000 μm, preferably >500 μm, more preferably >250 μm.

Process

Another object of the present invention is a method of processing an orodispersible tablets, comprising
(i) mixing the mucoadhesive active composition of the present invention and excipients to obtain a mixture, wherein the excipients comprise at least one disintegrant,
(ii) compressing the mixture of step (i) to obtain orodispersible tablets.

In one preferred embodiment the mucoadhesive active granules is with a diameter between about 50 and about 1,000 μm, preferably between about 75 and about 700 μm, more preferably between about 100 and about 600 μm, and even more preferably about 500 μm.

In another preferable embodiment the excipients are firstly sieved to obtain small particular excipients with diameter with a diameter <500 μm, preferably <400 μm, more preferably <200 μm.

The orodispersible tablet produced through the method of the present invention is preferably in a weight of 20-1000 mg.

And the orodispersible tablet produced through the method of the present invention is preferably with a diameter of 5-18 mm, more preferably with a diameter of 10 mm.

Another object of the present invention is to provide a system for testing a mucoadhesive formulation and quantify its mucoadhesion, more particularly a system for testing the mucoadhesion of a formulation, comprising
(i) a metal-cell comprising a bottom part (1), a parafilm (2), a metal disc (3) and a fixing ring (4);
(ii) a first container comprising a support part (5) inside and a top cover (6) with a pore (7), wherein the height of the support part (5) is bigger than the half height of the first container (B) and the upper surface of the support part (5) is big enough to support the metal-cell (A); wherein
(iii) the metal-cell (A) lies on the upper surface of the support part (5), and the pore (7) is direct above the metal-cell (A).

In one preferable embodiment the system further comprises a second container (C) including a top cover (8) with a pore (9) and a pump (D), which are via a pipe (10) passing through the pores (7) and (9) connected with the first container (B).

In another preferable embodiment according to the invention a water bath (E) is arranged to keep the first container (B) and the second container (C) at a suitable temperature of about 37° C.

Another object of the present invention is a method of testing the mucoadhesion of a dosage form, wherein the method is carried on the system of the present invention, comprises the following steps:
(i) fixing a piece of mucosa (M) with the fixing ring (4) between the bottom part (1) and the para film (2) of the metal-cell (A), wetting of mucosa with artificial saliva and putting a mucoadhesive formulation (F) on the mucosa (M);
(ii) dropping the artificial saliva through the pore (7) to the mucoadhesive formulation (F) in the first container (B);
(iii) removing the mucosa (M) and the para film (2) from the metal-cell (A) and washing them with a dilute agent to determine the number of viable bacteria adhesive to the mucosa;
(iv) washing the rest parts of the metal-cell (A) with a dilute agent and combining with the added artificial saliva in the first container (B) to determine the number of viable bacteria washed off with the artificial saliva.

In the present invention the used mucosa is preferably a piece of porcine mucosa with a thickness of 1 to 5 mm and a diameter similar as that of the metal-cell (A).

The tested mucoadhesive formulation, or parts of it like one-fourth is usually with a weight of about 10-200 mg.

The used artificial saliva in the present invention is formulated to mimic natural saliva, but does not stimulate salivary gland activity.

In one preferable embodiment of the present invention the artificial saliva is pumped through the pipe (10) from the second container (C) to the mucoadhesive formulation (F) in the first container (B), wherein the pumping flow rate of the artificial saliva is from 0.05 ml/min to 1.0 ml/min, preferably from 0.1 ml/min to 0.5 ml/min and the pumping lasts 30 to 120 min, preferably 60 min.

In the present invention the number of viable bacteria adhesive to the mucosa or washed off with the artificial saliva was determined by colony-forming unit (CFU). CFU is a rough estimate of the number of viable bacteria or fungal cells in a sample.

With the testing method of the present invention the mucoadhesion of a series of formulations can be determined, comprising, but not limited to, solid formulations, such as tablet, dragée, capsule, granule, powder and chewing gum, sticks, liquid formulations, such as solution, suspension, emulsion, syrup, spray, foam and semi-solid formulations, such as ointment, gel, paste.

Preferably the composition or product to be tested according to the invention may be selected form the group consisting of toothpaste, tooth gel, tooth powder, tooth cleaning liquid, tooth cleaning foam, mouth wash, mouth spray, dental floss, chewing gum and lozenges.

Such compositions or products may contain abrasive systems (abrasive and/or polishing components) such as silicates, calcium carbonate, calcium phosphate, aluminum oxide and/or hydroxyl apatite, surfactants such as e.g. sodium lauryl sulfate, sodium lauryl sarcosinate and/or cocamidopropyl betaine, humectants such as glycerol and/or sorbitol, thickening agents, e.g. carboxy methyl cellulose, poly ethylene glycols, carrageenans and/or Laponite®, sweeteners such as saccharine, aroma and taste correcting agents for unpleasant taste impressions, taste modifying substances (e.g. inositol phosphate, nucleotides, e.g. guanosine monophosphate, adenosine monophosphate or other substances, e.g. sodium glutamate or 2-phenoxy propionic acid), cooling agents such as menthol derivates (e.g. L-mentyl lactate, L-menthyl alkyl carbonate, menthone ketals), icilin and icilin derivates, stabilizers and active agents such as sodium fluoride, sodium monofluoro phosphate, tin difluoride, quarter-nary ammonium fluorides, zinc citrate, zinc sulfate, tin pyrophosphate, tin dichloride, mixtures of different pyrophosphates, triclosane, cetyl pyridinium chloride, aluminum lactate, potassium citrate, potassium nitrate, potassium chloride, strontium chloride, hydrogen peroxide, aroma substances, sodium bicarbonate and/or smell correcting agents.

Chewing gums or dental care chewing gums may comprise a chewing gum base comprising elastomers, e.g. polyvinyl acetate (PVA), polyethylene, (low or medium molecular) polyiso butane (PIB), polybutadiene, isobutene/isoprene copolymers, polyvinyl ethyl ether (PVE), polyvinyl butyl ether, copolymers of vinyl esters and vinyl ethers, styrene/butadiene copoly-mers (SBR) or vinyl elastomers, e.g. based on vinyl acetate/vinyl laurate, vinyl acetate/vinyl stearate or ethylene/vinyl acetate and mixtures of the mentioned elastomers as e.g. example described EP 0 242 325, U.S. Pat. No. 4,518,615, 5,093,136, 5,266,336 5,601,858 or 6,986,709. Additionally chewing gum bases may contain further ingredients, e.g. (mineral) filers, e.g. calcium carbonate, titanium dioxide, silicone dioxide, talcum, aluminum oxide, dicalcium phosphate, tricalcium phosphate, magnesium hydroxide and mixtures thereof, plasticisers (e.g. lanolin, stearic acid, sodium stearate, ethyl acetate, diacetin (glycerol diace-tate), triacetin (glycerol triacetate) and trietyhl citrate), emulsifiers (e.g. phosphatides, such as lecithin and mono and diglycerides of fatty acids, e.g. glycerol monostearate), antioxidants, waxes (e.g. paraffine waxes, candelilla waxes, carnauba waxes, microcrystalline waxes and polyethylene waxes), fats or fatty oils (e.g. hardened (hydrogenated) plant or animal fats) and mono, di or triglycerides.

By using the testing system and the method according to the present invention the mucoadhesion of various formulations can be easily, stably and at low cost determined and the obtained results possess high accuracy and good repeatability.

Another object of the present invention is a use of the system of the present invention for testing the mucoadhesion of a formulation.

EXAMPLES

Example 1

Preparation of a Mucoadhesive Orodispersible Tablet Comprising Mucoadhesive (Metolose 65SH50) Probiotic (*Lactobacillus plantarum* 299V) Granules.

Preparation of Mucoadhesive Probiotic Granules.

Firstly *Lactobacillus* planta rum 299v (LP299V®) was sieved to remove the particles with a diameter >200 µm. Then the sieved LP299V® and Metolose 65SH50 were added in a Turbula-Mixer and mixed at 30 r/min with the addition of desiccant bags for 5 min to obtain a dry homogeneous mixture, which was subsequently transferred into a Somakon Labmixer and tempered to 20° C. under flow of dry nitrogen. 5 ml Eudragit L isopropanol solution (12.5%) was added into the mixture under stirring at 280 r/min and then the wetted mixture was stirred for 1 min using the scrapper as well before the rest Eudragit L isopropanol solution was added under stirring at 330 r/min. After stirring at 370 r/min for 2 min with the scrapper the wetted granules formed and were sieved through a 710 µm sieve, then put into a desiccator and flushed with compressed air till the water activity of the granules reached <0.1. The obtained dry granules were sieved through a 500 µm sieve to obtain mucoadhesive probiotic granules.

Preparation of a Mucoadhesive Orodispersible Tablet.

Firstly the mixture of Syloid® 244 FP and AL-1FP Silicas (1:1), flavour Optamint® Lemon-Lime and Avicel® PH 112 were separately sieved through a 315 µm sieve and mixed together with Pearlitol® 100 SD and Kollidon® CL-SF. Then the mixture was added into a Turbula-Mixer to the mucoadhesive granules obtained in step (1) plus sieved Pruv® and mixed at 30 r/min adding the desiccant bags for 10 min to obtain a dry homogeneous mixture. Before the tablet compression the housing surrounding the tablet stamps of the single punch machine was flushed with compressed air till the humanity was less than 15%. Then 200 mg final mixture was added into the die mould and the mixture was compressed to obtain a mucoadhesive orodispersible tablet Ex1. The characterization data of the tablet were concluded in Table 5. The amount of each material is listed in Table 1.

TABLE 1

Composition of tablet

| Compound | Amount (mg) |
| --- | --- |
| *Lactobacillus plantarum* 299V | 35 |
| Metolose 65 SH 50 | 10 |
| the mixture of Syloid ®244 FP and AL-1FP Silicas (1:1) | 20 |
| Flavour Optamint ® Lemon-Lime | 1 |
| Pruv ® | 1 |
| Avicel ®PH 112 | 90 |
| Pearlitol ® 100 SD | 31.5 |
| Kollidon ®CL-SF | 10 |

Comparative Example C1

Firstly LP299V° was mixed with Metolose 65SH50 for 10 min in Turbula mixer at 30 r/min using desiccant bag (pre-mix). The mixture of Syloid® 244 FP and AL-1FP Silicas (1:1), flavour Optamint® Lemon-Lime and Avicel® PH 112 were separately sieved through a 315 µm sieve and mixed together with Pearlitol® 100 SD and Kollidon® CL-SF. The pre-mixing with the bacteria was added and another 10 min mixed in Turbula mixer under the same conditions. Finally sieved Pruv® was added and 5 min mixed. The final mixture was as in Example 1 pressed into a comparative mucoadhesive orodispersible tablet Cp1. The characterization data of the tablet were concluded in Table 4.

Example 2

Preparation of a Mucoadhesive Orodispersible Tablet Comprising Mucoadhesive (Metolose 65SH50) Probiotic (*Lactobacillus paracasei* 8700:2) Granules.

The preparation steps were the same as that of Example 1, but without sieving of the bacterial powder prior to granulation. The amount of each material is listed in Table 2.

TABLE 2

Composition of tablet

| Compound | Amount (mg) |
|---|---|
| Lactobacillus plantarum 299V | 35 |
| Metolose 65 SH 50 | 10 |
| the mixture of Syloid ®244 FP and AL-1FP silicas (1:1) | 20 |
| Flavour Optamint ® Lemon-Lime | 1 |
| Pruv ® | 1 |
| Avicel ®PH 112 | 90 |
| Pearlitol ® 100 SD | 31.5 |
| Kollidon ®CL-SF | 10 |

In Example 2 a mucoadhesive orodispersible tablet Ext was obtained and the characterization data of the tablet were concluded in Table 4.

Comparative Example C2

The preparation steps were the same as that of Comparative Example 1. And the amount of each material is listed in Table 2. In Comparative Example 2 a mucoadhesive orodispersible tablet Cp2 was obtained and the characterization data of the tablet were concluded in Table 4.

Example 3

Preparation of a Mucoadhesive Orodispersible Tablet Comprising Mucoadhesive (Chitosan Food Grade) Probiotic (Lactobacillus paracasei 8700:2) Granules.

The preparation steps were the same as that of Example 1, but without sieving of the bacterial powder prior to granulation. The amount of each material is listed in Table 3.

TABLE 3

Composition of tablet

| Compound | Amount (mg) |
|---|---|
| Lactobacillus plantarum 299V | 35 |
| Chitosan food grade | 26 |
| the mixture of Syloid ®244 FP and AL-1FP Silicas (1:1) | 20 |
| Flavour Optamint ® Lemon-Lime | 1 |
| Pruv ® | 1 |
| Avicel ®PH 112 | 73.7 |
| Pearlitol ® 100 SD | 31.5 |
| Kollidon ®CL-SF | 10 |

In Example 3 a mucoadhesive orodispersible tablet Ex3 was obtained and the characterization data of the tablet were concluded in Table 4.

Comparative Example C3

The preparation steps were the same as that of Comparative Example 1. And the amount of each material is listed in Table 3. In Comparative Example 3 a mucoadhesive orodispersible tablet Cp3 was obtained and the characterization data of the tablet were concluded in Table 4.

Characterization

The Friability of the samples was tested according to the EUROPEAN PHARMACOPOEIA 8.2, capture 2.9.7.

The Breaking strength of the samples was tested according to the EUROPEAN PHARMACOPOEIA 8.2, capture 2.9.8.

The Disintegration time of the samples were tested according to the EUROPEAN PHARMACOPOEIA 8.2, capture 2.9.1.

Uniformity of mass of single-dose preparations was tested according to the EUROPEAN PHARMACOPOEIA 8.2, capture 2.9.5.

The corresponding data was listed in the following Table 4.

TABLE 4

Characterization data

| Nr. | Average mass | Uniformity of mass | Friability [%] | Breaking strength [N] | Water activity | Disintegration time [s] |
|---|---|---|---|---|---|---|
| Ex1 | 200.7 | Confirms | 0.78 | 51.38 | 0.023 | 18.07 |
| Cp1 | 200.4 | Confirms | 0.78 | 44.0 | 0.038 | 42.8 |
| Ex2 | 199.5 | Confirms | 0.96 | 47.8 | 0.064 | 12.56 |
| Cp2 | 200.5 | Confirms | 0.99 | 49.3 | 0.038 | 45.52 |
| Ex3 | 202.2 | Confirms | 0.82 | 47.1 | 0.049 | 20.32 |
| Cp3 | 201.2 | Confirms | 0.65 | 54.4 | 0.052 | 26.7 |

The data in Table 4 show that, the tablets obtained in Examples 1, 2 and 3 according to the present invention exhibited shorter disintegration time than those in Comparative Examples 1, 2 and 3. These results demonstrate that the orodispersible tablets produced according to the invention, i.e. firstly mucoahesive active granules were produced and further processed into the orodispersible tablets, possess better characters compared with the tablets in the prior art.

Example 4

Preparation of a Mucoadhesive Orodispersible Tablet Comprising Mucoadhesive (Carbopol 971P NF) Probiotic (Lactobacillus plantarum HEAL9) by Freeze-Drying.

All excipients except Lactobacillus plantarum HEAL9 were mixed together to a homogenous suspension. Afterwards the thawed probiotic is added and stirred for 10 min to disperse the excipients homogenously. 500 µl of the formulation are pipetted into each blister well and were freeze dried for 22-24 h. The amount of each material for one tablet (lyophilisate) is listed in Table 5.

TABLE 5

Composition of tablet

| Compound | Amount (mg) |
|---|---|
| Lactobacillus plantarum HEAL9 Pellets | 57.8 |
| Carbopol ® 971P NF | 4.5 |
| Mannitol | 24.9 |
| Glucidex 6 ® D | 8.9 |
| Gelita ® Sol P | 4.1 |
| Highly purified water | 411.5 |

Comparative Example C4

Preparation of orodispersible tablet comprising probiotic (Lactobacillus plantarum HEALS) by freeze-drying. The preparation steps was the same as that of Example 4 and the amount of each material is listed in Table 6, but Carbopol was exchanged by water.

Example 5

Testing the Mucoadhesion of the Obtained Mucoadhesive Orodispersible Tablets

The mucoadhesion of the obtained mucoadhesive orodispersible tablets was tested on the system as follows:

(i) A piece of deep-frozen porcine mucosa with a thickness of about 2 mm and a diameter of 2.5 cm was prepared and put on the bottom part (1) of the metal-cell (A), then the para film (2) and the metal disc (3) were sequentially put on the mucosa. With the fixing ring (4) the mucosa was fixed in the metal-cell (A) and its surface was wetted with 2 or 3 drops of artificial saliva. The metal-cell (A) was put on the upper surface of the support part (5) in the first container (B), then a quarter of the obtained tablet from Examples and Comparative Examples (about 10-50 mg) was with a tweezer pressed on the mucosa.

(ii) The top cover (6) of the first container (B) was closed and the artificial saliva was at a rate of 0.1 or 0.5 ml/min pumped from the second container (C) to the tablet. The pumping was stopped after 60 minutes and the metal-cell (A) was removed from the first container (B).

(iii) The fixing ring (4) was released and with the metal disc (3) put back into the first container (B). Subsequently the mucosa and the para film (2) were removed with a tweezer from the bottom part (1) and put in the first sterilized glass beaker while the bottom part (1) was also put back into the first container (B). 100 g dilute agent (8.5 g/l sodium chloride, 1 g/l peptone, 10 ml/l Tween 80) was added into the glass beaker and the obtained solution A was magnetic stirred at 500 rpm for 30 min.

(iv) The artificial saliva in the first container (B) was firstly poured into the second sterilized glass beaker. Then 500 ml dilute agent (8.5 g/l sodium chloride, 1 g/l peptone) was used to wash the container (B) and the rest part of the metal-cell (A), and then also poured into the second sterilized glass beaker. By the addition of the dilute agent (8.5 g/l sodium chloride, 1 g/l peptone) the liquid in the glass beaker was added to 1000 g. The obtained solution B was magnetic stirred at 200 rpm for 5 min.

(v) Preparation of dilution series out of each glass beaker and enumeration of lactic acid bacteria.

The used artificial saliva was prepared according to Matzker/Schreiber 1972 (without $CaCl_2$) and its composition was listed in the following Table 6.

TABLE 6

| Artificial salva | |
|---|---|
| | Amount (g) |
| Constituent basic solution | |
| NaCl | 0.84 |
| KCl | 1.2 |
| $K_2HPO_4 \cdot 3H_2O$ | 0.34 |
| $H_2O$ | 1000 |
| HCl (1M) | Adjust pH to 6.9 |
| Addition to basic solution | |
| A-Amylase | 20.6 mg |
| Mucin | 10.0 mg |
| Basic solution | Ad 100.0 g |

The obtained solution A and B were respectively used to determine the number of viable bacteria adhesive to the mucosa and the number of viable bacteria washed off with the artificial saliva. The CFU was calculated with the following formula:

$$CFU/g = \frac{(N_{colonies} \times 1Edilution)}{M_{tablet}(g) \times 0.1)}$$

The results were shown in Table 7.

TABLE 7

| | Viable bacteria | | |
|---|---|---|---|
| No. | CFU/g of Solution A (mucosa) | CFU/g of Solution B (flushed away) | Adhesion (%) |
| Ex1 | 9.3E+9 | 2.1E+10 | 35 |
| Cp1 | 2.4E+10 | 1.1E+10 | 32 |
| Ex2 | 7.8E+9 | 6.2E+9 | 46 |
| Cp2 | 5.0E+9 | 1.1E+10 | 24 |
| EX3 | 8.9E+9 | 4.6E+9 | 46 |
| Cp3 | 3.7E+9 | 1.1E+10 | 21 |
| Ex4 | 7.5E+10 | 3.5E+10 | 53 |
| Cp4 | 2.7E+10 | 1.8E+11 | 12 |

The data in Table 7 showed that, the active probiotics constitute of the tablets obtained in Examples 1, 2, 3 and 4 adhered easier to the mucosa in comparison with those in Comparative Examples 1, 2, 3 and 4. The addition of mucoadhesive polymers results in higher mucoadhesion of the bacteria, because only 10% of probiotics remain on the mucosa after the test using tablets without mucoadhesive polymer. Examples and the Comparative Examples 1, 2, 3 show higher mucoadhesion than 10%, because they include mucoadhesive polymers. The positive effect of mucoadhesive polymers becomes also clear in Example 4 in contrast to Comparative Example 4 (without mucoadhesive polymer). Moreover the granulation of the bacteria with mucoadhesive polymers results in higher mucoadhesion (Examples 1-3) compared to just mixing of the excipients (Comparative Examples 1-3).

The invention claimed is:

1. A method of treating the oral cavity of a person having gingivitis or periodontitis with an orodispersible tablet, wherein the orodispersible tablet consists of a
    (a) mucoadhesive active composition in the form of granules having a diameter of from 50 to 1000 μm and, consisting of
    (a1) a mucoadhesive polymer selected from group consisting of polyacrylic acid, hypromellose and chitosan, and
    (a2) a probiotic which is selected from the group consisting of *Lactobacillus plantarum* 299V, *Lactobacillus plantarum* Heal 9, *Lactobacillus plantarum* Heal 52A, *Lactobacillus plantarum* Heal 99, *Lactobacillus fermentum* 35 D, *Lactobacillus fermentum* GOS 51, *Lactobacillus plantarum* GOS 42, and *Lactobacillus paracasei* GOS 63, and
    (a3) a binder selected from the group consisting of acacia gum, gelatin, polyvinylpyrrolidone, copovidone, polyvinyl alcohol, starch, alginate derivatives, sorbitol, sugars, tragacanth, methylcellulose, hydroxypropylmethylcellulose, sodium carboxymethylcellulose, hydroxypropylcellulose, maltodextrin, ammonio methacrylate copolymer, methacrylic acid methyl methycrylate copolymer, basic butylated methacrylate copolymer, methacrylic acid ethyl acrylate copolymer, cellacefate, hypromellose acetate succinate, hypromellose phthalate, polyvinyl acetate phthalate, polyvinyl alcohol-polyethylene glycol copolymer, and shellac in an amount of from 0.5 to 20 wt. %, based on the weight of the probiotic, and (b) at least one disintegrant selected from the group consisting of croscarmellose sodium, calcium carboxymethyl cellulose, crospovidone, sodium starch glycolate, alginic acid, calcium alginate, bentonite, cellulose, and guar galactomannan in an amount of from about 1 to about 15 wt. % based on the weight of the orodispersible tablet and;

wherein the method consists of:

mixing the components (a) and (b) into a dry homogenous mixture wherein the ratio between the mucoadhesive polymer and the probiotic is from abut 10:1 to about 1:50 and compressing the mixture to form an orodispersible tablet applying the orodispersible tablet to the oral cavity of the person having gingivitis or periodontitis, and allowing the orodispersible tablet to dissolve completely in the oral cavity within 3 minutes, and wherein the probiotic is retained on the oral mucosa of the oral cavity of the person having gingivitis or periodontitis by the mucoadhesive polymer for a period sufficient to treat the gingivitis or periodontitis.

2. The method of claim 1, wherein the mucoadhesive active composition is present in an amount of 0.1 to about 80% by weight of the tablet.

3. The method of claim 1, wherein the orodispersible tablet has a disintegration time of less than 30 seconds and a mucoadhesion of viable bacteria from the probiotic to an oral mucous membrane of the oral cavity of greater than 32% based on the total amount of viable bacteria in the probiotic.

4. The method of claim 3, wherein the level of oral mucoadhesion to an oral mucous membrane of viable bacteria from the probiotic is ≥35% based on the total amount of viable bacteria in the probiotic.

5. The method of claim 1 wherein the mucoadhesive polymer is selected from group consisting of polyacrylic acid, and chitosan.

* * * * *